US011377420B2

(12) United States Patent
Doyle et al.

(10) Patent No.: US 11,377,420 B2
(45) Date of Patent: Jul. 5, 2022

(54) COMPOSITIONS AND METHODS FOR MAKING DONOR-ACCEPTOR AZETINES

(71) Applicant: Board of Regents, The University of Texas System, Austin, TX (US)

(72) Inventors: Michael Patrick Doyle, San Antonio, TX (US); Kostiantyn Oleksandrovich Marichev, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/910,582

(22) Filed: Jun. 24, 2020

(65) Prior Publication Data
US 2020/0399214 A1 Dec. 24, 2020

Related U.S. Application Data

(60) Provisional application No. 62/865,525, filed on Jun. 24, 2019.

(51) Int. Cl.
| C07D 205/06 | (2006.01) |
| B01J 31/22 | (2006.01) |
| C07J 41/00 | (2006.01) |
| C07C 229/46 | (2006.01) |
| C07D 219/12 | (2006.01) |

(52) U.S. Cl.
CPC ............ *C07D 205/06* (2013.01); *B01J 31/22* (2013.01); *C07C 229/46* (2013.01); *C07D 219/12* (2013.01); *C07J 41/0055* (2013.01); *B01J 2531/16* (2013.01)

(58) Field of Classification Search
None
See application file for complete search history.

(56) References Cited

U.S. PATENT DOCUMENTS 8,889,857 B2    11/2014 Bruno et al.

FOREIGN PATENT DOCUMENTS

WO    2013/184198 A1    12/2013

OTHER PUBLICATIONS

Grant& Hackh's Chemical Dictionary (5th Ed. 1987) at p. 148.*
Barluenga, et al., Copper(I)-Catalyzed [3+1] cycloaddition of Alkenyldiazoacetates and Iminoiodinances: Easy Access to Substituted 2-Azetines. Chemistry—A European Journal, 2012, 18, 9221-9224.*
Adalsteinsson et al., "What Is the Mechanism of Catalysis of Ester Aminolysis by Weak Amine Bases? Comparison of Experimental Studies and Theoretical Investigation of the Aminolysis of Substituted Phenyl Esters of Quinoline-6- and-8-Carboxylic Acids," J. Am. Chem. Soc., 120, 3440-3447 (1998).
Barluenga et al., "Copper(I)-Catalyzed [3+1] Cycloaddition of Alkenyldiazoacetates andlminoiodinanes: Easy Access to Substituted 2-Azetines," Chem.—Eur. J , 18, 9221-9224 (2012).
Baumann et al., "Methods for the Synthesis of Substituted Azetines," Org. Lett., 19, 5681-5684 (2017).
Bizet et al., "Light-Induced Ruthenium-Catalyzed Nitrene Transfer Reactions: A PhotochemicalApproach towards N-Acyl Sul," Angew. Chem. Int. Ed., 53, 5639-5642 (2014).
Burkhard et al., "2,6-Diazaspiro[3.3]heptanes: Synthesis and Application in Pd-Catalyzed Aryl Amination Reactions," Org. Lett., 10, 3525-3526 (2008).
Burkhard et al., "Synthesis and Structural Analysis of a New Class of Azaspiro[3.3]heptanes as Building Blocks for Medicinal Chemistry," Org. Lett. 12, 1944-1947 (2010).
Burkhard et al., "Synthesis of Azaspirocycles and their Evaluation in Drug Discovery," Angew. Chem. Int. Ed., 49, 3524-3527 (2010).
Crowder et al., "Metallo-(Beta)-lactamases: Novel Weaponry for Antibiotic Resistance in Bacteria," Acc. Chem. Res., 39, 721-728 (2006).
Dejaegher et al., "The Chemistry of Azetidin-3-ones, Oxetan-3-ones, and Thietan-3-ones," Chem. Rev., 102, 29-60 (2002).
Deng et al., "Catalytic Asymmetric [3+1]-Cycloaddition Reaction of Ylides with ElectrophilicMetallo-enolcarbene Intermediates," Angew. Chem. Int. Ed., 56, 7479-7483 (2017).
Deng et al., "Catalytic Asymmetric Synthesis of Cyclopentyl (Beta)-Amino Esters by [3+2]Cycloaddition of Enecarbamates with Electrophilic MetalloenolcarbeneIntermediates," Angew. Chem. Int. Ed., 55, 10108-10112 (2016).
Deng et al., "Dinitrogen extrusion from enoldiazo compounds under thermal conditions: synthesis of donor-acceptor cyclopropenes," Chem. Commun., 65, 12924-12927 (2015).
Dong et al., "Recent Advances in Electrochemical Oxidative Cross-Coupling for the Construction of C—S Bonds," Synlett., 30(10): 1149-1163 (2019).
Elsharif et al., "Structure-Odor Relationship Study on Geraniol, Nerol, and Their Synthesized Oxygenated Derivatives," J Agric. Food Chem., 66, 2324-2333 (2018).
Fawcett et al., "Carbopalladation of C—C s-bonds enabled by strained boronate complexes," Nat. Chem., 11, 117-122 (2019).
Fawcett et al., "Strain-Release-Driven Homologation of Boronic Esters: Application to the Modular Synthesis of Azetidines," J. Am. Chem. Soc., 141, 4573-4578 (2019).
Fisher et al., "Bacterial Resistance to (Beta)-Lactam Antibiotics: Compelling Opportunism, Compelling Opportunity," Chem. Rev., 105, 395-424 (2005).

(Continued)

*Primary Examiner* — Po-Chih Chen
(74) *Attorney, Agent, or Firm* — Smith Gambrell Russell LLP; Judy Jarecki-Black; Ram W. Sabnis

(57) ABSTRACT

A highly effective synthetic route to produce donor-acceptor azetines through the highly enantioselective [3+1]-cycloaddition of silyl-protected enoldiazoacetates with aza-ylides using chiral copper(I) catalysis is provided. In one embodiment, the 2-azetidine cycloaddition products undergo generation of 3-azetidinones by reactions with nucleophiles that produce a broad spectrum of peptide products by the retro-Claisen reaction provided by facile strain with high efficacy and complete retention of enantiopurity. This ring opening reaction uncovers a new methodology for the attachment of chiral peptide units to a variety of amines and alcohols, and tolerates a broad scope of nucleophiles including naturally occurring amines, alcohols, amino acids, and other nitrogen based nucleophiles.

12 Claims, 5 Drawing Sheets

(56) References Cited

OTHER PUBLICATIONS

Gianatassio et al., "Strain-release amination," Science, 351, 241-246 (2016).
Gilchrist et al., "The Chemistry of Sulfilimines," C. J. Chem. Rev., 77, 409-435 (1977).
Hayashi et al., "Metal-Free Benzylic C—H Amination via Electrochemically GeneratedBenzylaminosulfonium Ions," Chem—Eur. J, 23, 61-64 (2017).
Hodgson et al., "Generation and Electrophile Trapping of N-Boc-2-lithio-2-azetine: Synthesis of 2-Substituted 2-Azetines," Org. Lett., 16, 856-859 (2014).
Hodgson et al., Lithiation-Electrophilic Substitution of N-Thiopivaloylazetidine,: J. Angew. Chem. Int. Ed., 49, 2900-2903 (2010).
Jukic et al., "Recent Advances in the Retro-Claisen Reaction and Its Synthetic Applications," Curr. Org. Synth., 9, 488-512 (2012).
Kamath et al., "Advances in the chemistry of B-lactam and its medicinal applications," Tetrahedron, 68, 10640-10664 (2012).
Kobayashi et al., "New Strategies for Fluorescent Probe Design in Medical Diagnostic Imaging," Chem. Rev., 110, 2620-2640 (2010).
Lavis et al., "Bright Building Blocks for Chemical Biology," ACS Chem. Biol., 9, 855-866 (2014).
Lavis et al., "Bright Ideas for Chemical Biology," ACS Chem. Biol., 3, 142-155 (2008).
Lee et al., "Peptide-Based Probes for Targeted Molecular Imaging," Biochemistry, 49, 1364-1376 (2010).
Lei et al., "Pharmacological Properties of Geraniol—A Review," Planta Med., 85, 48-55 (2019).
Lian et al., "Computationally Guided Stereocontrol of the Combined C—H Functionalization/Cope Rearrangement," Angew. Chem. Int. Ed., 50, 9370-9373 (2011).
Lopchuk et al., "Strain-Release Heteroatom Functionalization: Development, Scope, and Stereospecificity," J. Am. Chem. Soc., 139, 3209-3226 (2017).
Lopez et al., "Substituent Effects on Rates and Torquoselectivities of Electrocyclic Ring-Openings of N-Substituted 2-Azetines," J. Org. Chem., 79, 6189-6195 (2014).
Mangelinckx et al., "Experimental and Computational Study of the Conrotatory Ring Opening of Various 3-Chloro-2-azetines," J. Org. Chem., 73, 5481-5488 (2008).
Pang et al., "Intermolecular [2 + 2] Cycloaddition/Isomerization of Allenyl Imides and Unactivated Imines for the Synthesis of 1-Azadienes Catalyzed by a Ni(Cl04)2•6H2O Lewis Acid," ACS Catal, 8, 5193-5199 (2018).
Pazos et al., "Peptide-based fluorescent biosensors," Chem. Soc. Rev., 38, 3348-3359 (2009).
Qian et al., "Rhodium(II)- and Copper(II)-Catalyzed Reactions of Enol Diazoacetates withNitrones: Metal Carbene versus Lewis Acid Directed Pathways," Angew. Chem. Int. Ed., 51, 5900-5903 (2012).
Shawali et al., "Aminolysis of Esters. I. Kinetics and Mechanism in Anhydrous Dioxane," J. Am. Chem. Soc., 89, 3020-3026 (1967).
Shindoh et al., "Catalyst-Controlled Torquoselectivity Switch in the 4(Pi) Ring-Opening Reaction of 2-Amino-2-azetines Giving (Beta)-Substituted (Alpha, Beta)-Unsaturated Amidines," J. Am. Chem. Soc., 133, 8470-8473 (2011).
Smith et al., "Rhodium-Catalyzed Enantioselective Vinylogous Addition of Enol Ethers to Vinyldiazoacetates," J. Am. Chem. Soc, 134, 18241-18244 (2012).
Staderini et al., "Peptides for optical medical imaging and steps towards therapy," Bioorg. Med. Chem., 26, 2816-2826 (2018).
Tian et al., "Sulfilimines as Versatile Nitrene Transfer Reagents: Facile Access to Diverse Aza-Heterocycles," Angew. Chem. Int. Ed., 58, 3589-3593 (2019).
Wang et al., "Enantioselective Carbene Cascade: An Effective Approach to Cyclopentadienes and Applications in Diels-Alder Reactions," Adv. Synth. & Catal., 358, 1571-1576 (2016).
Xu et al., "A donor-acceptor cyclopropene as a dipole source for a silver(I) catalyzed asymmetric catalytic [3+3]-cycloaddition with nitrones," Chem. Commun., 49, 10287-10289 (2013).
Xu et al., "Straightforward Access to the [3.2.2]Nonatriene Structural Framework via Intramolecular Cyclopropenation/Buchner Reaction/ Cope Rearrangement Cascade," Org. Lett., 17, 790-793 (2015).
Xu et al., "Synthesis of Tetrahydropyridazines by a Metal-Carbene-Directed EnantioselectiveVinylogous N—H Insertion/LewisAcid-Catalyzed Diastereoselective MannichAddition," Angew. Chem. Int. Ed., 51, 9829-9833 (2012).
Yoshimura et al., "Preparation and Physical and Chemical Properties of "Free" Sulfilimines," J. Org. Chem., 41, 1728-1733 (1976).
Zhu et al., "Gold-Catalyzed Formal [4+1 ]/[4+3] Cycloadditions of Diazo Esters with Triazines," Angew. Chem. Int. Ed., 55, 11867-11871 (2016).
Degl'Innocenti, A., et al., "Allylsilanes by the regio- and stereocontrolled substitution of metalated homoallylsilanes", Synlett, 3: 155-156(1991).
Dong, K., et al., "Role of donor-acceptor cyclopropenes in metal carbene reactions. Conversion of E-substituted enoldiazoacetates to Z-substituted metallo-enolcarbenes", Organometallics, 38:4043-4050 (2019).
Gamage, S.A, et al., "Aromatic annulation with naphtho[1,8-de]-1,3-dithiin carbocations", Tetrahedron, 46:2111-2128 (1990).
Klusener, P.A.A., et al., "On the direct metalation of isoprene", Tetrahedron, 47:2041-2064 (1991).
Moyer, M.P., et al., "Intramolecular N—H, O—H, and S—H insertion reactions. Synthesis of heterocycles from a-diazo ß-keto esters", J. Org. Chem., 50: 5223-5230 (1985).
Reich, H.J., et al., "Stereochemistry of a cyclohexyllithium reagent. A case of higher configurational stability in strongly coordinating media", J. Am. Chem. Soc., 114: 11003-11004 (1992).
Stanetty, P., et al., "Directed ortho lithiation of phenylcarbamic acid 1,1-dimethylethyl ester (N—BOC-aniline). Revision and improvements", J. Org. Chem., 57: 6833-6837 (1992).

\* cited by examiner 4
95%, 90% ee[a]

5
96%[a]

6
R = Bn 6a (93%, 90% ee)[b]
R = 4-Br-Bn 6b (85%)[b]

7
92%[a]

8
84%, 90% ee[a]

9
88%, 97% ee[a]

10
88% (single diastereomer)[c]

11
90% (single diastereomer)[c]

12
92%[a]

13
Ar = Ph 13a (65%)[d]
Ar = 4-NMe$_2$-C$_6$H$_4$ 13b (93%)[e]

14
84% (single diastereomer)[c]

15
63%[a]

23
66%, 90% ee[b]

24
62%[c]

25
48%[d]

26
70%[a]

27
Ar = Ph 27a (87%)[b]
Ar = 4-NO$_2$-C$_6$H$_4$ 27b (88%)[e]

28
93%[c]

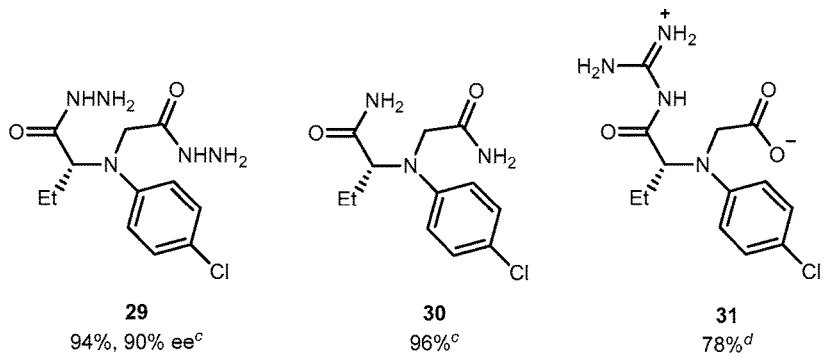
FIG. 3E  FIG. 3F  FIG. 3G
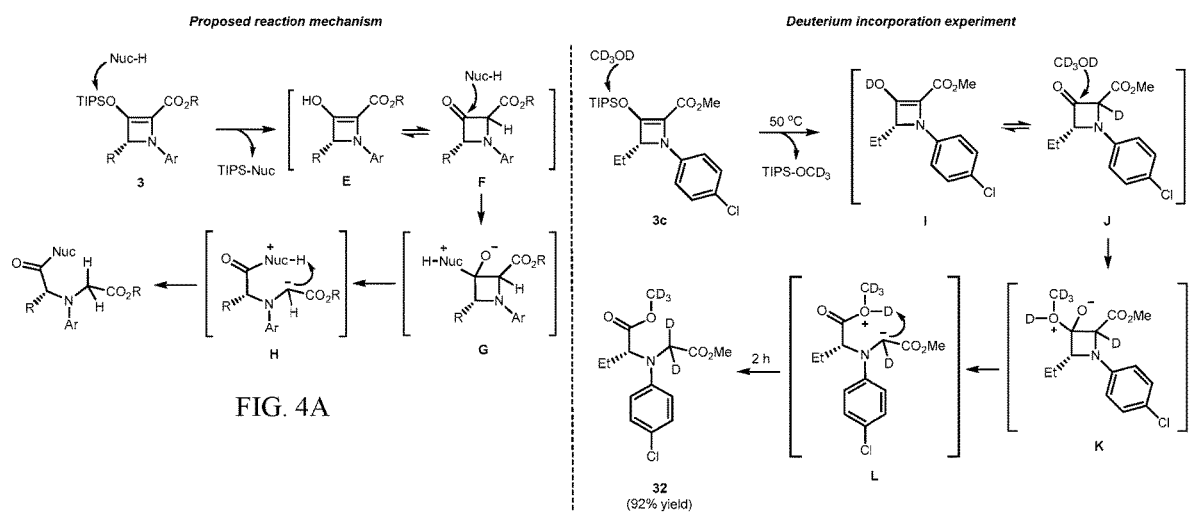
FIG. 4A
FIG. 4B
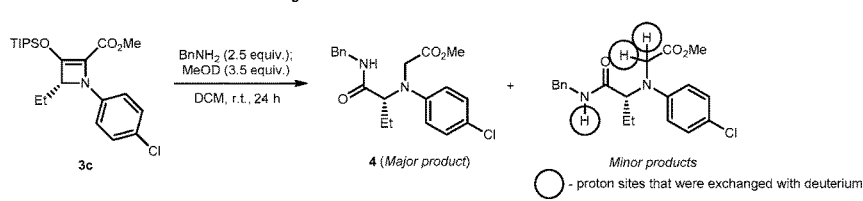
FIG. 4C

COMPOSITIONS AND METHODS FOR MAKING DONOR-ACCEPTOR AZETINES

CROSS-REFERENCE TO RELATED APPLICATIONS

This application claims benefit of and priority to U.S. Provisional Application No. 62/865,525 filed on Jun. 24, 2019, which is incorporated by reference in its entirety.

STATEMENT REGARDING FEDERALLY SPONSORED RESEARCH

This invention was made with government support under CHE-1559715 awarded by the National Science Foundation. The government has certain rights in the invention.

TECHNICAL FIELD OF THE INVENTION

Aspects of the invention are generally directed to the field of chemistry, in particular the synthesis of novel chiral donor—acceptor azetines.

BACKGROUND OF THE INVENTION

Coupling reactions of amines and alcohols are of central importance for applications in chemistry and biology. These transformations typically involve the use of a reagent, activated as an electrophile, onto which nucleophile coupling results in the formation of a carbon-nitrogen or a carbon-oxygen bond. Several promising reagents and procedures have been developed to achieve these bond forming processes in high yields with excellent stereocontrol, but few offer direct coupling without the intervention of a catalyst.

Irreversible ring opening of the strained 2-azetidinone four-membered ring, which is one of the key biomolecular events during both the antibiotic action of β-lactams and their inhibition by β-lactamases (Fisher, J. F. et al., *Chem. Rev.* 105, 395-424 (2005)), is a model for nucleophile coupling. The chemically controlled ring opening of 2-azetidinones with cleavage of the carbonyl-nitrogen bond is a powerful tool for the synthesis of heterocycles, 3-amino acids, and their derivatives (Palomo C. & Oiarbide M. (2010) In: Banik B. (eds) Heterocyclic Scaffolds I. Topics in Heterocyclic Chemistry, vol 22. Springer, Berlin, Heidelberg Page MI The chemistry of β-lactams. Chapman and Hall, London); Crowder, M. W. et al., *Acc. Chem. Res.*, 39, 721-728 (2006); Kamath, A. & Ojima, I., *Tetrahedron*, 68, 10640-10664 (2012)). Their versatility in chemistry and biology has propelled them to high levels of scientific and pharmacological importance. 3-Azetidinones, by contrast, are less well established (Dejaegher, Y., et al., *Chem. Rev,* 102, 29-60 (2002)) even though they have the potential for nucleophilic carbonyl-carbon cleavage to form amine derivatives (Eq. 1) if an activating electron-withdrawing group (EWG) is located at the 2-position; but the key to realizing this potential lies in the design of a 3-azetidinone capable of nucleophile coupling.

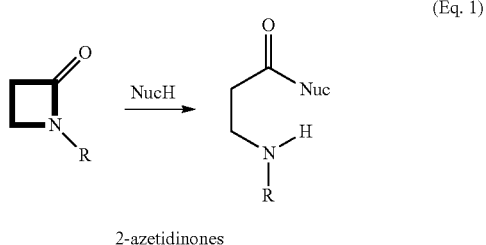

2-azetidinones

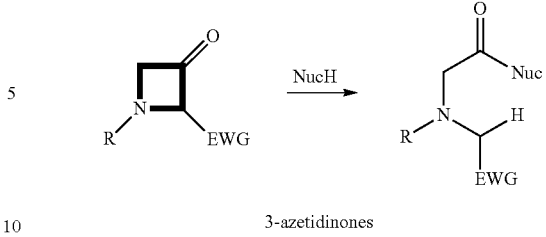

3-azetidinones

A classic approach to nucleophile coupling is the retro-Claisen reaction of β-ketoesters (Jukic, M., et al. *Curr. Org. Synth.* 9, 488-512 (2012)) that would require the construction of previously unreported 2-carboxylate substituted 3-azetidinones, but the basic methods available for their formation are the same as those desired for their ring-opening coupling which is favoured by ring strain (Gianatassio, R. et al. *Science,* 351, 241-246 (2016); Lopchuk, J. M. et al. *J. Am. Chem. Soc.,* 139, 3209-3226 (2017); Fawcett, A., et al., *Nat. Chem.,* 11, 117-122 (2019); Fawcett, A., et al., *J. Am. Chem. Soc.,* 141, 4573-4578 (2019)). Alternative methodologies proceeding to 2-azetine-2-carboxylate structures were applied to the formation of the 3-azedidinone analogues, either through [2+2]-cycloaddition (Pang, S. et al., *ACS Catal.* 8, 5193-5199 (2018)), from 3-substituted 2-azetines (lithiation) (Hodgson, D. M. & Kloesges, *J. Angew. Chem. Int. Ed.* 49, 2900-2903 (2010); Hodgson, D. M. et al., *Org. Lett.* 16, 856-859 (2014); Burkhard, J. A. & Carreira, E. M. *Org. Lett.* 10, 3525-3526 (2008); Burkhard, J. A. et al. *Angew. Chem. Int. Ed.* 49, 3524-3527 (2010); Burkhard, J. A. et al. *Org. Lett.* 12, 1944-1947 (2010)), or with N-Boc-3-azetidinone (coupling reactions) (Baumann, A. N. et al. *Org. Lett.* 19, 5681-5684 (2017)), but these methods were not suitable for 2-carboxylate derivatives. In addition, attempted copper(I)-catalyzed [3+1] cycloaddition of alkenyldiazoacetates and iminoiodinanes to form the requisite 3-azetidinone was also unsuccessful (Barluenga, J. et al. *Chem.—Eur. J.* 18, 9221-9224 (2012)).

Therefore, it is an object of the invention to provide new methods and reagents for producing donor-acceptor azetines.

SUMMARY OF THE INVENTION

A highly effective synthetic route to produce donor-acceptor azetines through the highly enantioselective [3+1]-cycloaddition of silyl-protected enoldiazoacetates with azaylides using chiral copper(I) catalysis is provided. In one embodiment, the 2-azetidine cycloaddition products undergo generation of 3-azetidinones by reactions with nucleophiles that produce a broad spectrum of peptide products by the retro-Claisen reaction provided by facile strain with high efficacy and complete retention of enantiopurity. This ring opening reaction uncovers a new methodology for the attachment of chiral peptide units to a variety of amines and alcohols, and tolerates a broad scope of nucleophiles including naturally occurring amines, alcohols, amino acids, and other nitrogen-based nucleophiles.

One embodiment provides a method for producing amino acid derivatives from donor-acceptor azetines by their selective coupling with nitrogen and oxygen nucleophiles via 3-azetidinones to form amino acid derivatives.

Another embodiment provides a method for synthesizing donor-acceptor azetines, by reacting an enoldiazoacetate with an aza-ylide in the presence of a copper catalyst to produce a donor-acceptor azetine. In another embodiment the aza-ylide includes, but is not limited to N-arylsulfilimine. In still another embodiment, the copper catalyst includes, but is not limited to $Cu(MeCN)_4PF_6$.

In some embodiments, the method includes a modified sidearm bisoxazoline (sabox) ligand.

Another embodiment provides a compound according to the following formula:

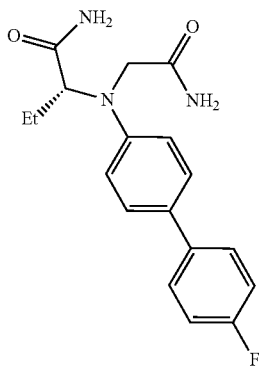

(33)

Another embodiment provides a compound according to the following formula:

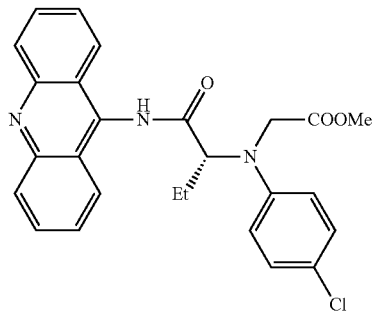

(34)

Another embodiment provides a compound according to the following formula:

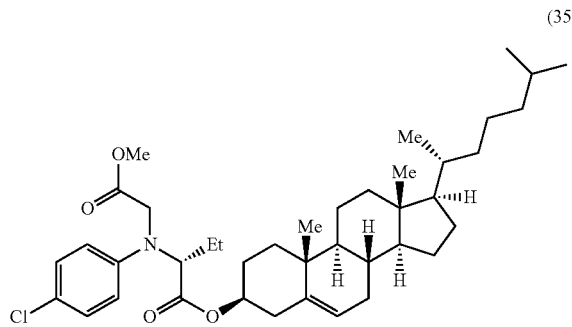

(35)

Still another embodiment provides a compound according to the following formula:

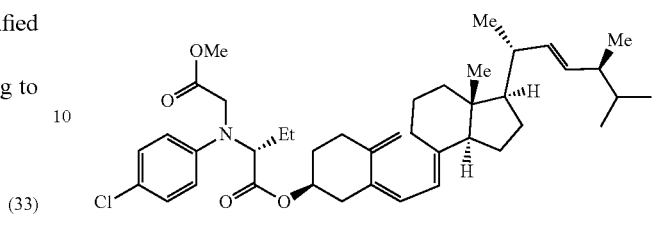

(36)

BRIEF DESCRIPTION OF THE DRAWINGS

FIGS. 3A-3G shows a panel of compounds synthesized using ring opening reactions of 2-azetine-2-carboxylate 3c with other nucleophiles. Reaction conditions: [a]0.2 mmol of 3, 0.3 mmol of TBAF, 4.0 mL of DCM, r.t., 2 h; [b]0.2 mmol of 3, 0.6 mmol of phenylhydrazine, 4.0 mL of DCE, 50° C., 12 h; [c]0.2 mmol of 3, 1.0 mmol of the nucleophile, 4.0 mL of THF, r.t., 12 h; [d]0.2 mmol of 3, 0.8 mmol of guanidine, 4.0 mL of THF/water 1:1 (v/v), r.t., 12 h; [e]0.2 mmol of 3, 0.6 mmol of 4-nitrophenylhydrazine, 3.0 mL of $MeNO_2$, r.t., 24 h.

FIG. 4A shows a proposed reaction mechanism for nucleophilic ring opening of 2-azetine-2-carboxylates 3. FIG. 4B shows a deuterium incorporation experimental scheme. FIG. 4C shows a proton-deuterium exchange with MeOD scheme.

DETAILED DESCRIPTION OF THE INVENTION

I. Definitions

Figure 1A:
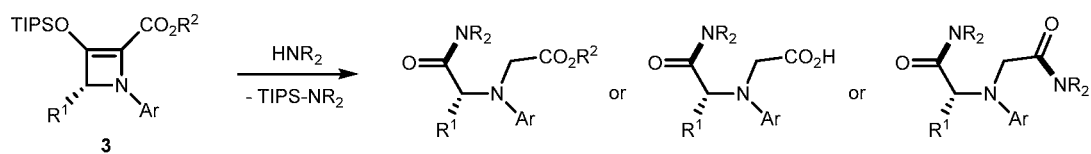
FIGS. 1A-1Q shows a panel of chiral peptides using ring opening reactions of 2-azetine-2-carboxylates 3 with amines. Reaction conditions: [a]0.2 mmol of 3, 0.5 mmol of amine, 4.0 mL of DCM, r.t., 48 h; [b]0.2 mmol of 3, 0.8 mmol of amine, 4.0 mL of THF/water 1:1 (v/v), r.t., 12 h; [c]0.2 mmol of 3, 0.5 mmol of amine, 4.0 mL of DCM, r.t., 4 days; [d]0.2 mmol of 3, 0.6 mmol of amine, 4.0 mL of DCE, 65° C., 24 h; [e]0.2 mmol of 3, 0.6 mmol of amine, 3.0 mL of MeNO2, r.t., 12 h.
Figure 1B:
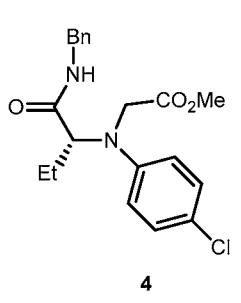
Figure 1C:
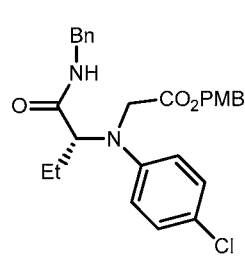
Figure 1D:
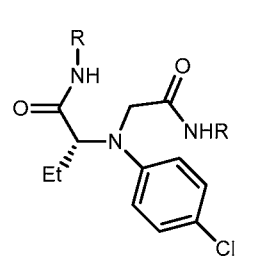
Figure 1E:
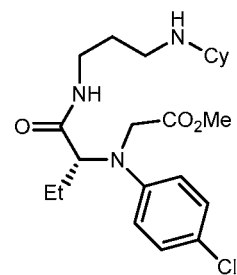
Figure 1F:
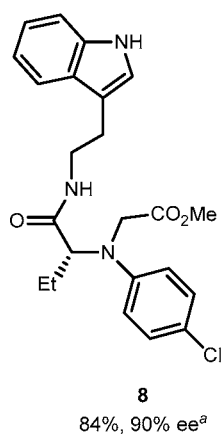
Figure 1G:
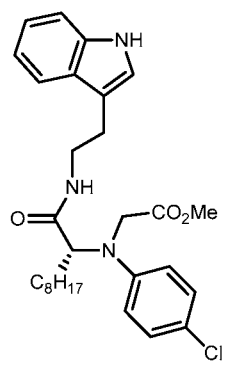
Figure 1H:
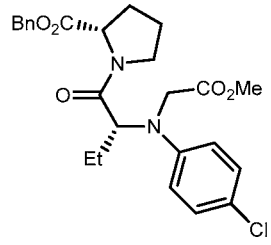
Figure 1I:
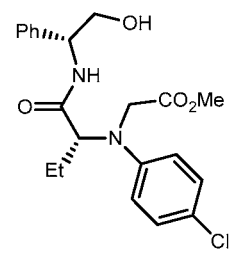
Figure 1J:
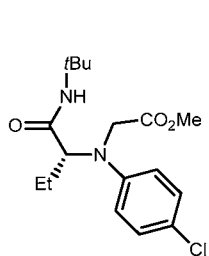
Figure 1K:
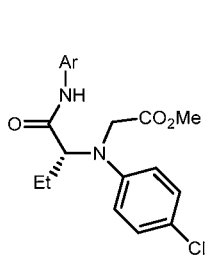
Figure 1L:
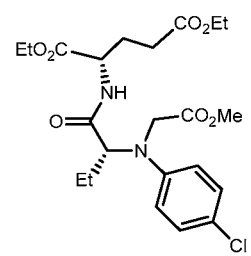
Figure 1M:
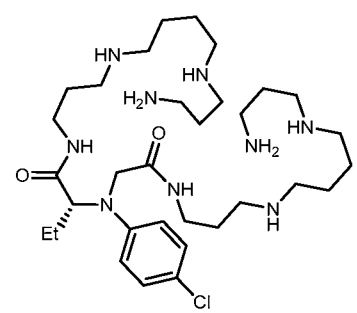

As used herein, the singular forms "a," "an," and "the" include plural referents unless the context clearly dictates otherwise. For example, reference to "the method of treatment" includes reference to equivalent steps and methods known to those skilled in the art, and so forth.

Recitation of ranges of values herein are merely intended to serve as a shorthand method of referring individually to each separate value falling within the range, unless otherwise indicated herein, and each separate value is incorporated into the specification as if it were individually recited herein.

The term "carrier" refers to an organic or inorganic ingredient, natural or synthetic, with which the active ingredient is combined to facilitate the application.

The term "pharmaceutically acceptable" means a non-toxic material that does not interfere with the effectiveness of the biological activity of the active ingredients.

The term "pharmaceutically-acceptable carrier" means one or more compatible solid or liquid fillers, diluents or encapsulating substances which are suitable for administration to a human or other vertebrate animal.

The term "effective amount" or "therapeutically effective amount" means a dosage sufficient to provide treatment a disorder, disease, or condition being treated, or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "subject," and "patient" are used interchangeably herein, and refer to a mammal, including, but not limited to, humans, rodents, such as mice and rats, and other laboratory animals.

II. Ring-Opened Products from Donor-Acceptor Azetine Compounds

Ring-opened products from donor-acceptor azetine compounds and methods of making the same are provided herein. Exemplary compounds are disclosed below.

A. Compounds

In one embodiment, ring-opened products from donor-acceptor azetine compounds are synthesized by ring opening reactions of 2-azetine-2-carboxylates 3 with amines. In one embodiment such compounds are selected from the group consisting of:

4a
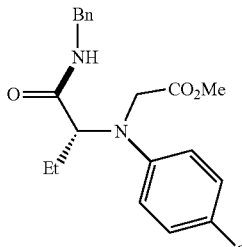

4b
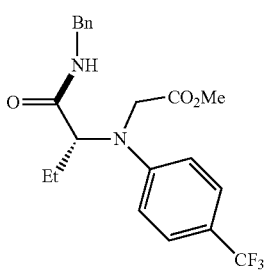

4c
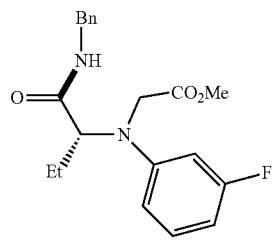

4d
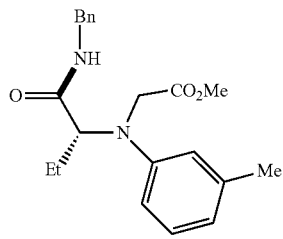

5
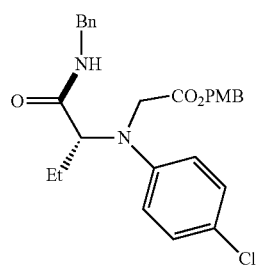

6
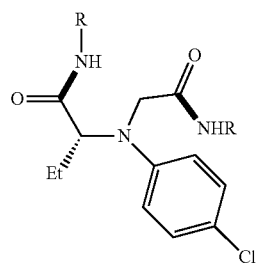

7
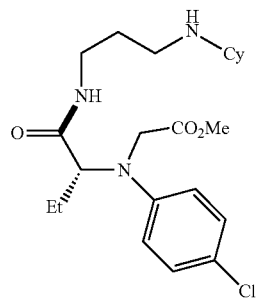

8
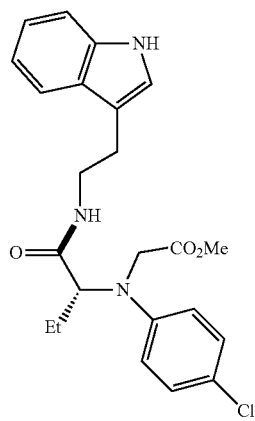
9
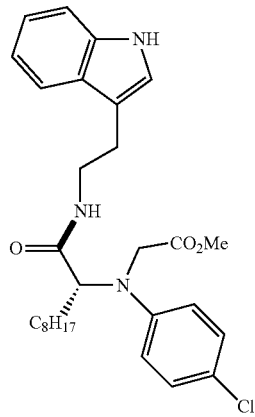
10
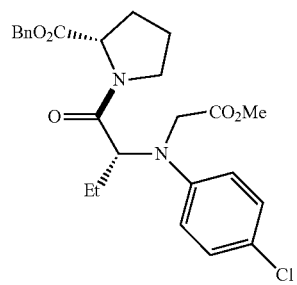
11
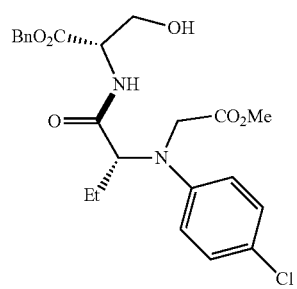
12
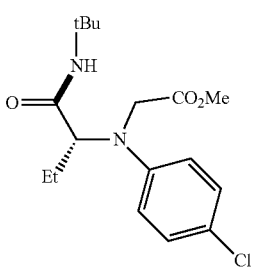
13
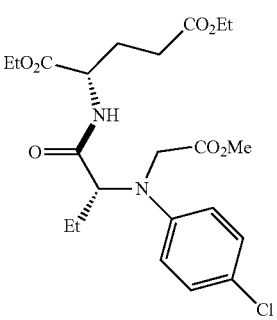
14
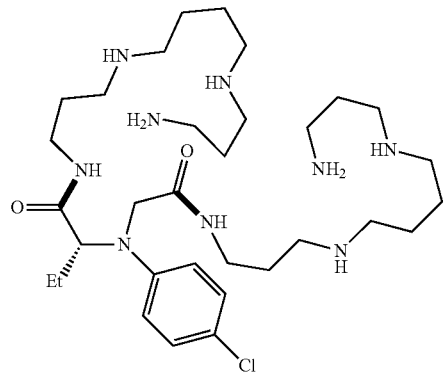
15
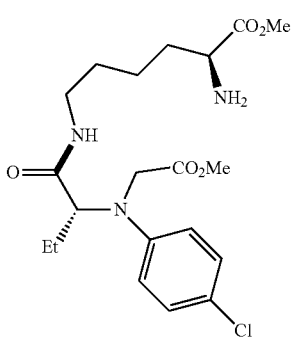
16

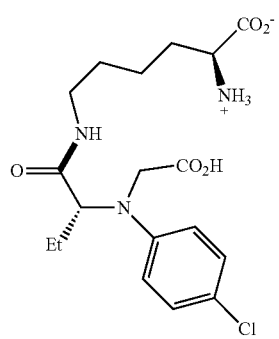

17

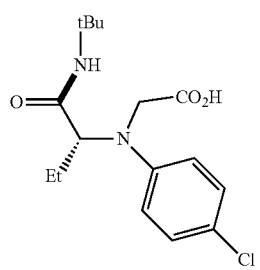

18

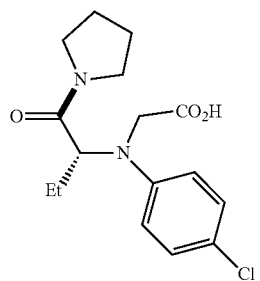

19

In another embodiment, ring-opened products from donor-acceptor azetine compounds are synthesized by ring opening reactions of 2-azetine-2-carboxylates 3 with alcohols. In one embodiment such compounds are selected from the group consisting of:

20

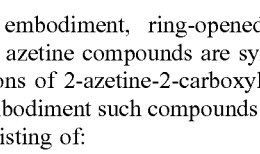

21

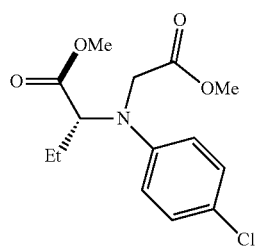

22

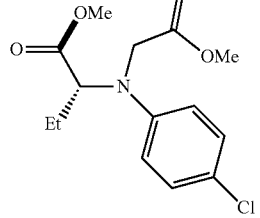

23

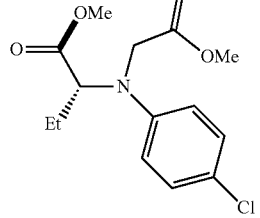

24

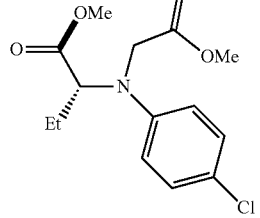

25

Another embodiment provides ring-opened products from donor-acceptor azetine compounds that are synthesized by ring opening reactions of 2-azetine-2-carboxylates 3c with other nucleophiles. In one embodiment such compounds are selected from the group consisting of:

26
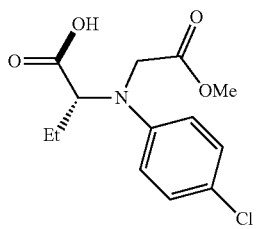

27
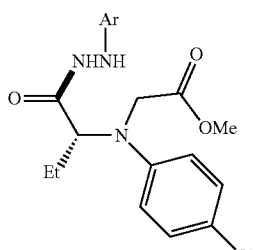

28
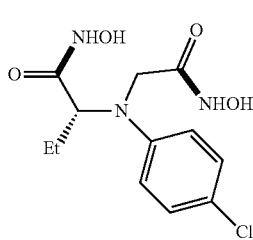

29
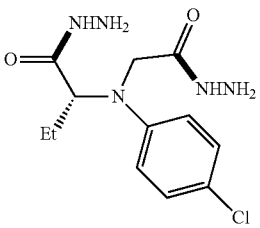

30
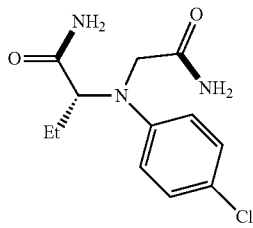

31
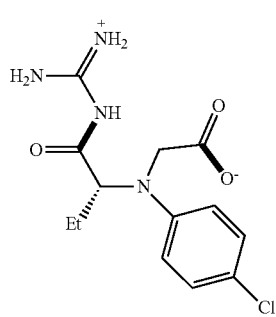

1. Conjugates

Some embodiments provide conjugates of the disclosed ring-opened products from donor-acceptor azetine compounds wherein the ring-opened products from donor-acceptor azetine compounds is conjugated to a second compound including but not limited to targeting moieties, proteins, peptides, antibodies, probes, markers, or labels. The moieties can be conjugated to the compounds to serve as detection agents, to deliver the compounds to specific cells or tissues, to deliver the compounds to specific subcellular locations, or a combination thereof.

In one embodiment, the disclosed ring-opened products from donor-acceptor azetine compounds are conjugated to one or more detection agents. Exemplary detection agents include but are not limited to fluorophores, isotope markers, colorimetric labels, biotin/avidin, fluorogens, or mass tags.

One embodiment provides ring-opened products from donor-acceptor azetine compounds containing fluorine atoms that are synthesized through Suzuki-Miyaura $sp^2$-$sp^2$ cross-coupling with diamide. The compounds are as follows:

(33)
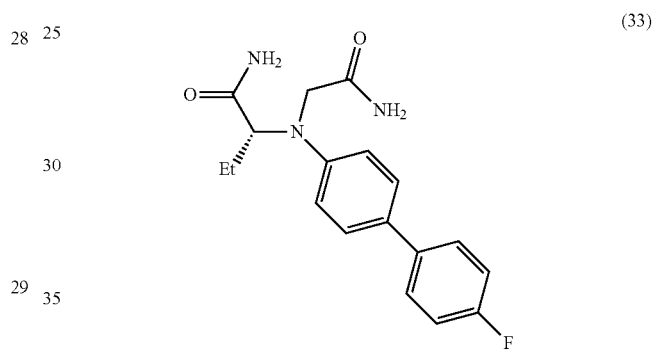

One embodiment provides ring-opened products from donor-acceptor azetine compounds conjugated to a fluorescent unit using the ring opening reaction of azetine 3c with 4-aminoacridine as a fluorophore-carrying nucleophile. The compounds are as follows:

(34)
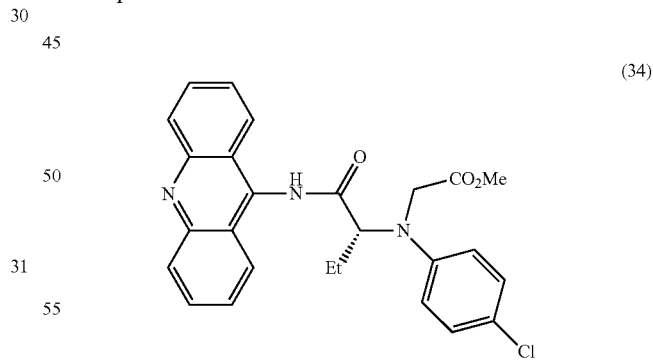

In one embodiment, the disclosed compounds are conjugated with a moiety that delivers the compounds to specific cells or tissues, or to specific subcellular locations. In such an embodiment, the compound is conjugated with a moiety that targets a protein or receptor that is present on the desired tissue, cell type, or subcellular location. In one embodiment, the moiety is an antibody that binds to a receptor on the target cell. In another embodiment, the moiety is a small molecule that binds to a receptor on the target cell. In yet another embodiment, the moiety a sugar molecule, a glycolytic enzyme, or folate. Exemplary compounds are as follows:

III (35)

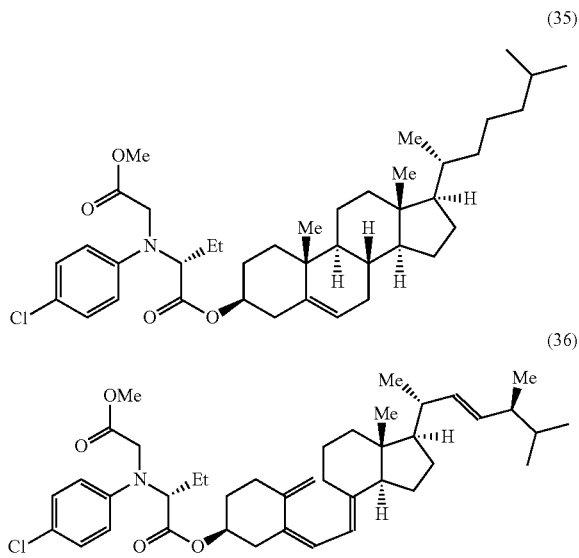

(36)

In one embodiment, the disclosed ring-opened products from donor-acceptor azetine compounds are conjugated to a biomolecule. In certain embodiments, the biomolecule includes but is not limited to a protein, antibody, small biomolecule, biotin, or biological ligands. The term "biological ligands" refers to protein receptors, lipid receptors, polysaccharide receptors, lipopolysaccharide receptors, glycolipids, and their biological ligands. The protein receptor can be intracellular or express on the cell surface.

III. Production of Ring-Opened Products From Donor-Acceptor Azetines

A. [3+1]-Cycloaddition: Reaction Development.

Application of N-acylimido sulfur ylides (Yoshimura, T. & Omata, T. J. Org. Chem. 41, 1728-1733 (1976); Bizet, V., et al. Angew. Chem. Int. Ed. 53, 5639-5642 (2014); Hayashi, R. et al. Chem.—Eur. J. 23, 61-64 (2017)) and enoldiazoacetates to the same catalysts and conditions that were successful with their carbon analogues was unsuccessful even at elevated temperatures due to a lack of reactivity of the imido ylide. Use of N-arylimido sulfur ylides (S,S-disubstituted N-arylsulfilimines) (Gilchrist, T. L. & Moody, C. J. Chem. Rev. 77, 409-435 (1977); Garcia Ruano, J. L. et al. Science of Synthesis, 39, 245-390 (2007); Tian, X. et al. Angew. Chem. Int. Ed., 58, 3589-3593 (2019)), however, allowed cycloaddition to proceed smoothly at room temperature. As previously described for the corresponding [3+1]-cycloaddition that formed donor-acceptor cyclobutene derivatives (Deng, Y., et al., Angew. Chem. Int. Ed. 56, 7479-7483 (2017)), only copper(I) catalysis was effective for this transformation; and $Cu(MeCN)_4PF_6$ was the catalyst of choice in the formation of 2-azetines. Product yields were the highest in dichloromethane, and diphenylsulfur ylides gave higher product yields than their dimethyl or methylphenyl analogues. Reactions were performed at room temperature to avoid electroreversion of the azetine (Lopez, S. A. & Houk, K. N. J. Org. Chem. 79, 6189-6195 (2014); Shindoh, N., et al., J. Am. Chem. Soc. 133, 8470-8473 (2011); Mangelinckx, S. et al. J. Org. Chem. 73, 5481-5488 (2008)). [3+1]-Cycloaddition occurred with the triisopropylsilyl(TIPS)-protected enoldiazoacetate but not with the tert-butyldimethylsilyl(TBS)-protected enoldiazoacetate. With these optimizations methyl N-(p-chlorophenyl)-3-OTIPS-2-azetine-2-carboxylate 3 was formed in 80% isolated yield (Eq. 2).

(Eq. 2)

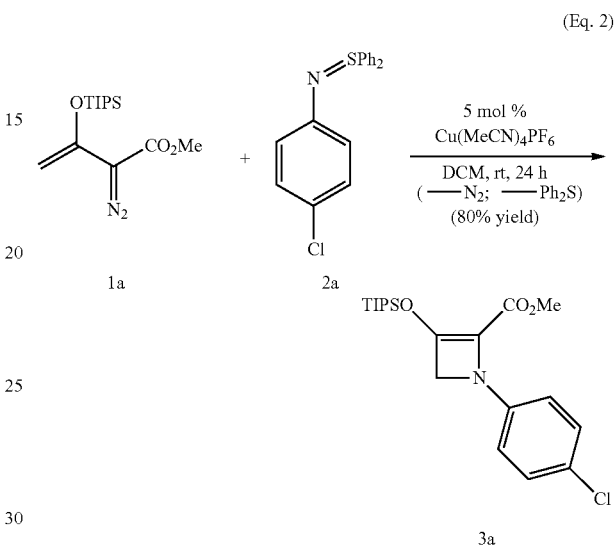

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

To introduce chirality into the 2-azetine-2-carboxylate a substituent at the terminal vinyl position of enoldiazoacetate 1 is required. Previous reports on enoldiazoacetates described the synthesis and uses of only two TBS- and TIPS-protected enoldiazoacetates having terminal vinyl substituents (4-Me and 4-Ar) (Deng, Y., et al., Angew. Chem. Int. Ed. 56, 7479-7483 (2017); Wang, X. et al. Adv. Synth. & Catal. 358, 1571-1576 (2016); Deng, Y., et al., Chem. Commun., 51, 12924-12927 (2015); Xu, X., et al., Org. Lett., 17, 790-793 (2015); Xu, X., et al., Chem. Commun., 49, 10287-10289 (2013); Qian, Y. et al., Angew. Chem. Int. Ed., 51, 5900-5903 (2012); Zhu, C., et al., Angew. Chem. Int. Ed., 55, 11867-11871 (2016); Lian, Y., et al., Angew. Chem. Int. Ed., 50, 9370-9373 (2011)), and both of their geometrical isomers were formed in the case of TIPS-derivatives. Provided herein is a synthetic solution to this challenge that allows dominant formation of the Z-isomer (Z:E=>20:1) for these substituted enoldiazoacetates (Dong, K., et al., Synlett, 30 (2019)) and, only the Z-isomer undergoes [3+1]-cycloaddition.

To effect asymmetric induction for 2-azetine ring formation, methyl (Z)-3-OTIPS-2-diazo-3-pentenoate 1b with N-(p-chlorophenyl)imido diphenylsulfur ylide 2a were initially selected and the cycloaddition reaction was performed under the optimized conditions with catalysis by $Cu(MeCN)_4PF_6$ coordinated to chiral sabox ligand L1 (Eq. 3).

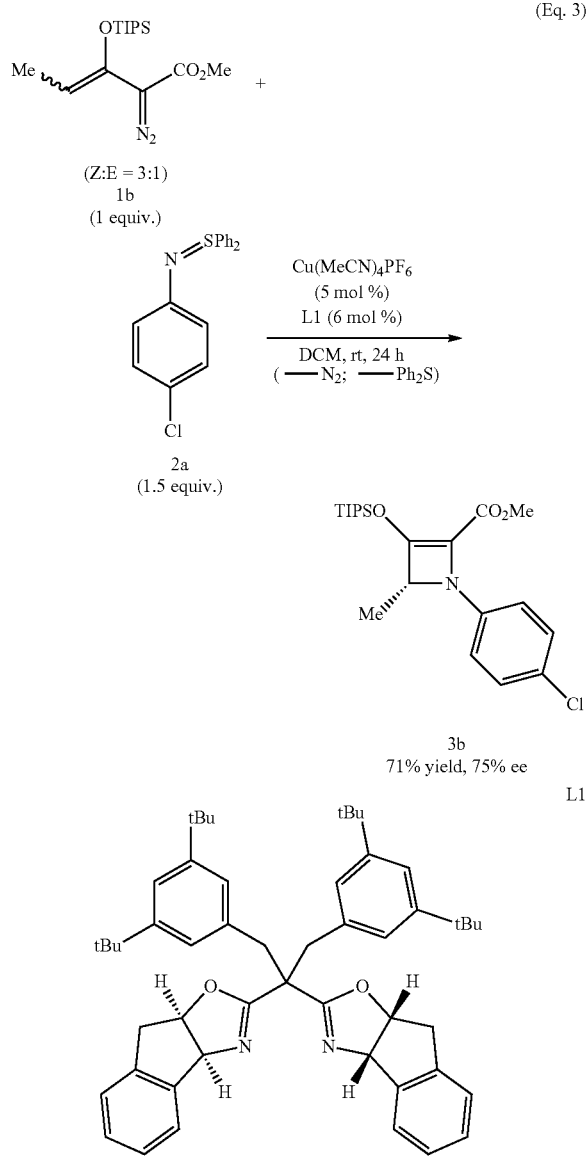

(Eq. 3)

3b
71% yield, 75% ee

L1

The use of ligand L1 resulted in the highest yield and enantioselectivity (71% yield, 75% ee). Although the yield and enantioselectivity for 3b obtained with L1 were only moderate, substituents were varied at the 4-position of enoldiazoacetate 1 in order to determine if these substituents influence product formation and selectivity. A general procedure was established for the introduction of substituents to the 4-position of enoldiazoacetate 1 (Dong, K., et al., Synlett, 30 (2019)); and, using 2a as the optimum sulfilimine, [3+1]-cycloaddition was performed under optimum conditions. The initial reaction of 1b (Z:E=3:1) with a 50% molar excess of 2a showed complete loss of Z-1b but retention of E-1b and a 75% ee for 3b (Eq. 3). This observation prompted the use of an excess of the 4-substituted enoldiazoacetate over sulfilimine 2a to reflect the actual stoichiometric amount of the Z-isomer in the Z-1/E-1 mixture. When the reaction of 1b (Z:E=>20:1) with 2a was repeated using a (1.2):1 ratio 1b/2a [vs. 1: (1.5) reported in Eq. 3], this modification resulted in an increased yield of 3b to 82% (entry 1, Table 1) with the same ee value of 75%.

Changing the methyl substituent at the 4-position of 1 to ethyl not only improved the enantioselectivity for the [3+1]-cycloaddition to 90% ee but also resulted in an increase of the isolated yield (92%) of 3c (entry 2, Table 1). Further elaboration of the substituent at the 4-position with benzyl (3d), isopropyl (3e), and n-octyl (3f) under the same conditions led to a modest decrease in reactivity, apparently due to steric effects, and lowered product yields, but % ee values were comparable to or higher than that of 3c (90-97% ee).

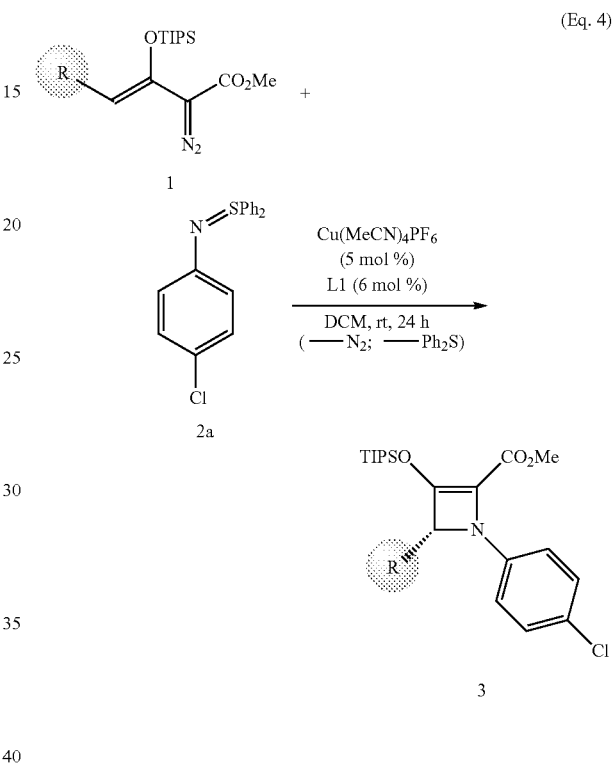

(Eq. 4)

TABLE 1

Scope of enoldiazoacetates: effect of the aliphatic chain at the 4-position of enoldiazoacetate 1

| entry[a] | R | yield 3 (%)[b] | ee (%)[c] |
|---|---|---|---|
| 1 | Me | 3b 82 | 75 |
| 2 | Et | 3c 92 | 90 |
| 3[d] | Bn | 3d 73 | 90 |
| 4[d] | iPr | 3e 70 | 92 |
| 5[d] | n-C$_8$H$_{17}$ | 3f 63 | 97 |

[a]All reactions were carried out on a 0.20 mmol scale in 4.0 mL DCM: 2a (0.20 mmol), 1a (0.24 mmol).
[b]Isolated yield after flash-chromatography.
[c]Determined by chiral HPLC analysis.
[d]Reaction time was 72 h.

To identify a possible further improvement in enantiocontrol the influence of the carboxylate ether group (size and electronic effects) of enoldiazoacetates 1 was investigated. With an Et ($R^1$) substituent at the 4-position (Table 2) introduction of an isopropyl group as $R^2$ (1g) resulted in a decrease of azetine yield without a change in enantioselectivity (entry 1; Table 2). Notably, the corresponding tert-butyl enoldiazoacetate ($R^2$=tBu) resulted in only trace amounts of the [3+1]-cycloaddition product. Neither benzyl (1h) nor 4-bromobenzyl (1i) substituted enoldiazoacetates provided any noticeable improvement in enantiocontrol (90-92% ee) and yields (87-90%) (entries 2,3; Table 2). Surprisingly, the p-methoxybenzyl (PMB) ester provided a remarkable level of enantiocontrol (99% ee) and also produced 3j in 95% yield (entry 4; Table 2). A very similar ee value (98% ee) was obtained for the 3,4,5-trimethoxybenzyl derivative 3k, however the reaction time for this reaction was extended to 48 h in order to achieve full conversion (entry 5; Table 2). As expected, the presence of the electron withdrawing $CF_3$ group at the 4-position of phenyl ring (1l) resulted in decrease of both the yield (73%) and enantioselectivity (87% ee) of azetine 3l. To determine that the effect of the PMB group as $R^2$ might be general p-methoxybenzyl 3-OTIPS-2-diazo-3-pentenoate 1m was prepared and the [3+1]-cycloaddition reaction was performed (entry 7; Table 2): enantioselectivity was improved from 75% (3b, $R^2$=Me) to 88% ee (3m, $R^2$=PMB).

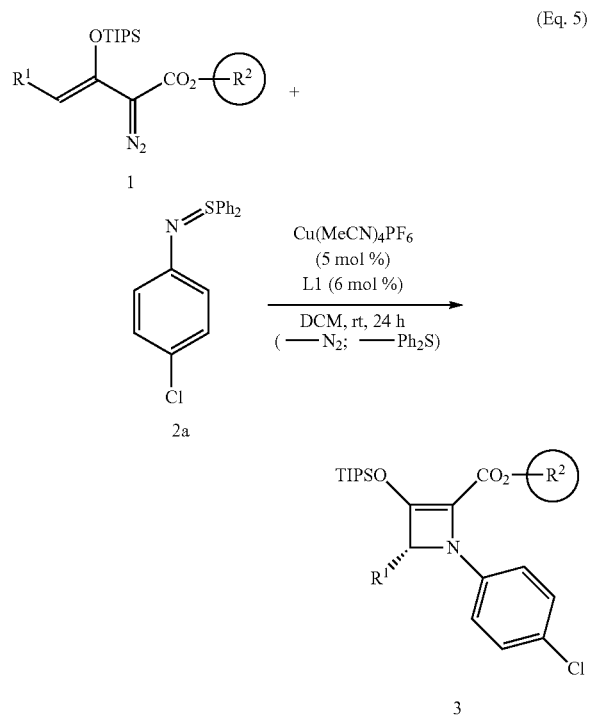

(Eq. 5)

TABLE 2

Scope of enoldiazoacetates: effect of the carboxylate group

| entry[a] | $R^1$ | $R^2$ | yield 3 (%)[b] | ee (%)[c] |
|---|---|---|---|---|
| 1 | Et | iPr | 3g 82 | 89 |
| 2 | Et | Bn | 3h 87 | 92 |
| 3 | Et | 4-BrBn | 3i 90 | 90 |
| 4 | Et | 4-OMeBn | 3j 95 | 99 |
| 5[d] | Et | 3,4,5-triOMeBn | 3k 70 | 98 |
| 6 | Et | 4-CF$_3$Bn | 3l 73 | 87 |
| 7 | Me | 4-OMeBn | 3m 77 | 88 |

[a]All reactions were carried out on a 0.20 mmol scale in 4.0 mL DCM: 2a (0.20 mmol), 1a (0.24 mmol).
[b]Isolated yield after flash-chromatography.
[c]Determined by chiral HPLC analysis.
[d]Reaction time was 48 h.

B. Nucleophilic Ring Opening Reactions of Donor-Acceptor Azetines.

That ring opening would be a facile process of these donor-acceptor azetines was not initially obvious. Five- and six-membered ring silyl-protected β-enolcarboxylates are well known to form 0-ketoesters after desilylation (Smith, A. G. & Davies, H. M. L., J. Am. Chem. Soc., 134, 18241-18244 (2012); Deng, Y., et al., Angew. Chem. Int. Ed., 55, 10108-10112 (2016); Xu, X., et al., Chem. Commun. 49, 10287-10289 (2013); Xu, X., et al., Angew. Chem. Int. Ed. 51, 9829-9833 (2012)). However, when azetine 3b was treated with the classic TBAF to effect desilylation, a mixture of ring opened products was obtained under typically mild conditions. This observation suggested that initial enolate formation had occurred and that subsequent nucleophilic reaction on the β-keto ester or its equivalent effected strain-induced ring opening. To determine the extent of nucleophilic ring opening with strain release of donor-acceptor azetines were treated with a variety of nitrogen and oxygen nucleophiles. It was assumed that TIPS group removal from 2-azetine-2-carboxylates 3 occurs under mild conditions to generate the 3-azetidinone carboxylate structure, which then undergoes ring opening with the excess of a nucleophile (Eq. 6). This concept of strain release through carbon-carbon σ-bond cleavage from 3-azetidinone carboxylates bond is uncovered in this work for the first time, and this nucleophile coupling opens doors to enormous opportunities in the synthesis of new chiral peptides and relevant substances of biological interest with high optical purity.

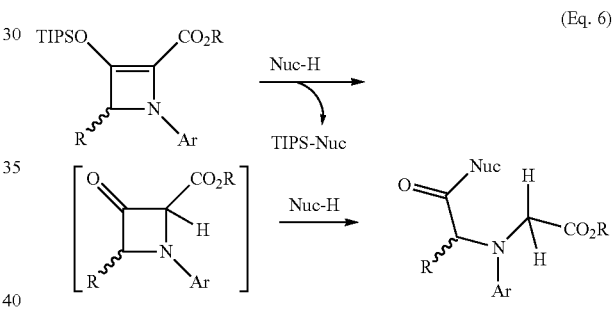

(Eq. 6)

Figures 1N, 1O, 1P, 1Q:
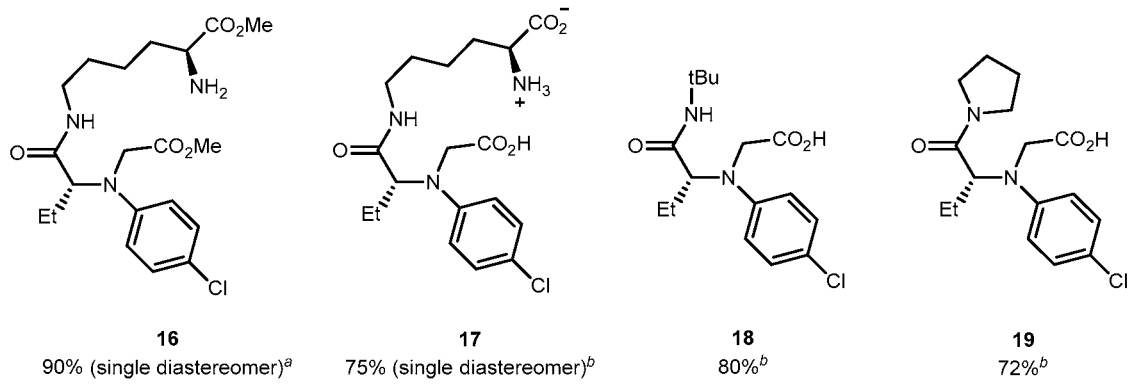

2-Azetine-2-carboxylates 3c and 3j were the substrates of choice in most cases because of their availability[26] and optical purity (90% and 99% ee, respectively). Initial assessment of reactivity was carried out by reactions with 2.5 equiv. of benzylamine in DCM at room temperature (FIGS. 1A-1P). Ring opened products that contain one peptide bond were formed within 48 h in near quantitative isolated yields (4, 95% and 5, 96%). Moreover, the complete retention of optical purity in the products of the nucleophile coupling reactions were observed. The ester functionality remained intact under these reaction conditions even when 4 equiv. of benzylamine was used. However, consistent with nucleophilic reactions that form ionic intermediates (Shawali, A. S. A. S. & Biechler, S. S., J. Am. Chem. Soc. 89, 3020-3026 (1967); Adalsteinsson, H. & Bruice, T. C., J. Am. Chem. Soc., 120, 3440-3447 (1998)), changing the polarity of the solvent played a significant role in increasing the reactivity of 3c towards benzylamine, so that with 4 equiv. of benzylamine or 4-bromobenzylamine in THF/water 1:1 (v/v) chiral diamide derivatives 6a,b were formed in high yields (93% and 85%, respectively) within 12 h. This was an unexpected observation because the classic reaction of an ester with amines is very sluggish at room temperature. A control reaction of monoamide 4 with an excess of benzylamine (2 equiv.) resulted in a quantitative yield of diamide 6 in 12 h. Apparently, formation of the first amide unit activates the carbonyl group of the ester via intramolecular hydrogen bonding in water (polar protic solvent), and therefore favors the nucleophilic substitution by benzylamine on the ester group. The regioselectivity of the ring opening reaction of 3c with N-cyclohexyl-1,3-propanediamine (primary-secondary diamine) was investigated. Formation of the amide bond occurred exclusively at the primary amine position of the diamine, and the monoamination product 7 was isolated in 92% yield. Inspired by the results with benzylamine, the remarkable levels of regioselectivity with N-cyclohexyl-1,3-propanediamine, and the solvent effect on product formation, reactions of 2-azetines 3c and 3f with biologically relevant amines and natural amino acids were examined. Monoamide derivatives of tryptamine (8 and 9), benzyl-protected L-proline (10), and glutamic acid diethyl ester (14), for example, were obtained in 84-88% isolated yields in reactions carried out in dichloromethane. Ring opening of 3c with a natural polyamine, spermine, in DCM occurred selectively at the terminal primary amine position of spermine but, unlike with other amines, formed chiral diamide 15 as the major product (63% yield). The reaction of 3c with tert-butylamine, a sterically hindered primary amine, occurred with similar efficacy as that with benzylamine (92% yield). Treatment of azetine 3c with aromatic amines, which are weaker nucleophiles, showed negligible conversion in DCM at room temperature, but heating 3c with aniline (3 equiv.) at 65° C. in 1,2-dichloroethane (DCE) for 24 h resulted in ring opening nucleophilic coupling; however, 13a was formed in only 65% yield together with the product from the known thermal electrocyclic ring opening of 3c (Lopez, S. A. & Houk, K. N., *J. Org. Chem.* 79, 6189-6195 (2014); Shindoh, N., et al., *J. Am. Chem. Soc.* 133, 8470-8473 (2011); Mangelinckx, S. et al. *J. Org. Chem.* 73, 5481-5488 (2008)). Use of electron-rich 4-(dimethylamino)aniline with 3c in nitromethane at room temperature increased the yield of the ring opened product to 93% (13b). The reaction of 3c with (R)-phenylglycinol (2.5 equiv.) in DCM at room temperature was sluggish but highly selective towards the amino group, affording monoamidation product 11 (d.r.>20:1) in 90% yield after 4 days. It was also determined if L-lysine methyl ester (basic form) was able to provide high regioselectivity in the ring opening reaction with 3c carried out in DCM. Indeed, remarkable regiocontrol (at the terminal amino group) was achieved in the formation of monoamide derivative 16 (90% yield of a single diastereomer). The same regiocontrol was obtained in the reaction of 2-azetine carboxylate 3c with L-lysine (4 equiv.) in THF/water 1:1 (v/v), but this reaction also resulted in hydrolysis of the ester to the carboxylic acid (17, 75% yield) under the reaction conditions. Reactions with tert-butylamine and pyrrolidine in THF/water 1:1 (v/v), unlike that with benzylamine, resulted in monoamidation and hydrolysis of the ester to form amidocarboxylic acids 18 (80%) and 19 (72%), rather than in the formation of a diamide.

Figure 2A:
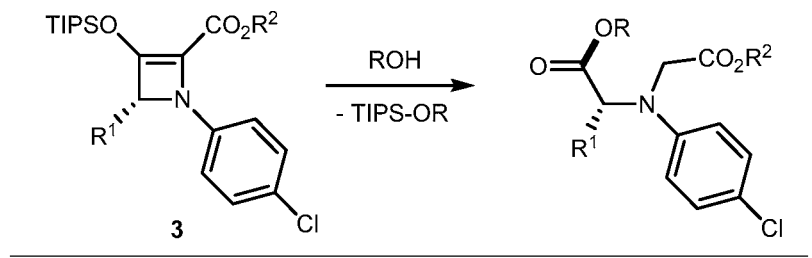
FIGS. 2A-2G shows a panel of chiral diesters synthesized using ring opening reactions of 2-azetine-2-carboxylates 3 with alcohols. Reaction conditions: [a]0.2 mmol of 3, 5.0 mL of MeOH, 65° C., 2 h; [b]0.2 mmol of 3, 5.0 mL of EtOH, 65° C., 24 h; [c]0.2 mmol of 3, 0.8 mmol of alcohol, 3.0 mL of THF, 65° C., 24 h; [d]0.2 mmol of 3, 0.8 mmol of alcohol, 3.0 mL of 1,4-dioxane/water 2:1 (v/v), 65° C., 24 h.
Figures 2B, 2C, 2D:
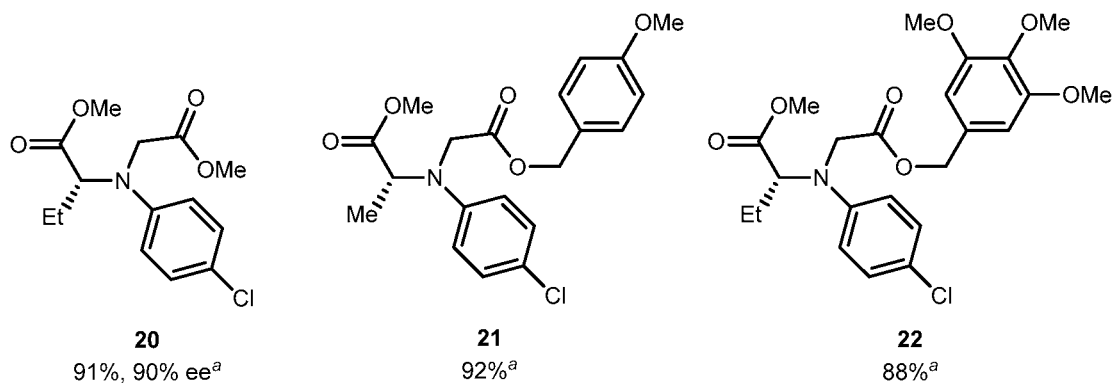
Figure 2E:
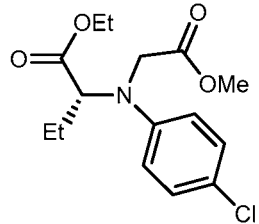
Figure 2F:
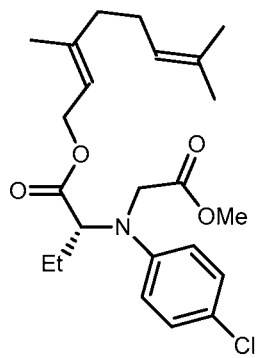
Figure 2G:
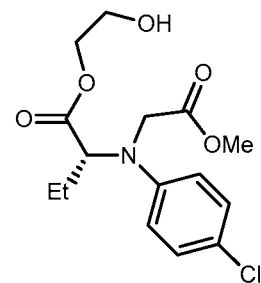
Figure 3A:
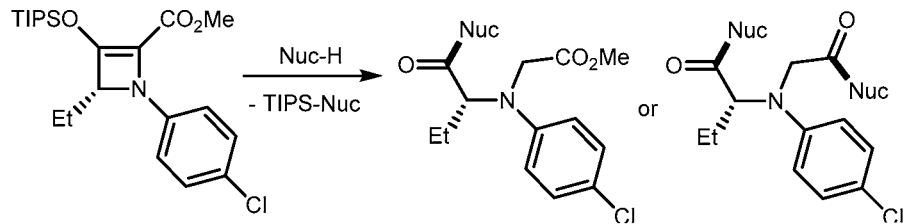
Figure 3B:
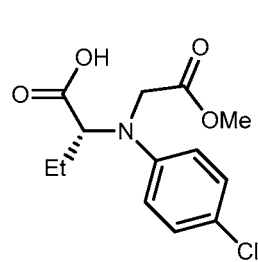
Figure 3C:
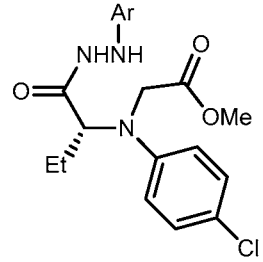
Figure 3D:
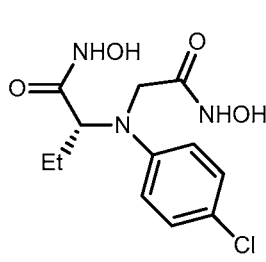

As expected, the ring opening reactions of 2-azetine-2-carboxylates with the weaker alcohol nucleophiles occurred at slower rates (FIG. 2A-). However, very high yields (up to 92%) of chiral diesters 20-22 were obtained with complete retention of enantiopurity from the reactions of 3c, 3j, and 3k with methanol used as the solvent at 65° C. Use of higher molecular weight primary alcohols resulted in a decrease of their reactivity with 2-azetine-2-carboxylates. The yield of diester 23 obtained with ethanol (66%) at 65° C. after 24 h was similar to that obtained from the reaction with aniline (65%) but a much larger excess of the nucleophile was used in this case (ethanol was used as the solvent). Geraniol (a naturally occurring primary alcohol) (Lei, Y., et al., *Planta Med.* 85, 48-55 (2019); Elsharif, S. A. & Buettner, A., et al., *J. Agric. Food Chem,* 66, 2324-2333 (2018)) and ethylene glycol also formed the corresponding diesters 24 and 25 in moderate yields at 65° C. after 24 h using only 4 equiv. of alcohol. In all reactions performed at elevated temperatures, the main competing reaction was electrocyclic ring opening of 2-azetine carboxylate 3c. (Lopez, S. A. & Houk, K. N., et al., *J. Org. Chem.* 79, 6189-6195 (2014); Shindoh, N., et al., *J. Am. Chem. Soc.,* 133, 8470-8473 (2011); Mangelinckx, S. et al.; *J. Org. Chem.,* 73, 5481-5488 (2008)).

Besides amines, amino acids, alcohols, other relatively strong nitrogen-based nucleophiles and tetrabutylammonium fluoride (TBAF) have been tested (FIG. 3). The monomethyl ester of chiral dicarboxylic acid 26 was obtained in 70% yield by a simple treatment of 2-azetine-2-carboxylate 3c with a THF solution of TBAF. Alternatively, compound 26 was obtained in near quantitative yield by treatment of azetine 3c with 5 equiv. of water in nitromethane at room temperature in 12 h. The reactivity of 3c with phenylhydrazine was higher than that with aniline, and chiral monohydrazide 27a was obtained in 87% yield at 50° C. in DCE after 12 h together with minor amounts (<10%) of the electrocyclic ring opening product from 3c. The reaction of electron-deficient 4-nitrophenylhydrazine with 3c in nitromethane at room temperature resulted in high yield (88%) of the ring opened product 27b. The use of aqueous solutions of hydroxylamine, hydrazine, and ammonia for the reaction with 3c in THF led to the formation of two C—N bonds and afforded chiral dihydroxamic acid 28, dihydrazide 29, and diamide 30 in excellent yields (up to 96%) in 12 h. Efforts to perform selective reactions leaving the ester group intact were not successful. An interesting example of guanidine-based chiral peptide 31 was obtained in the reaction of 3c with guanidine in THF/water 1:1 (v/v). Use of 4 equiv. of guanidine produced the zwitterionic peptide 27 in 78% isolated yield. The product of the attachment of two molecules of guanidine was detected in the reaction mixture by LC/MS but not isolated.

EXAMPLES

Example 1. Nucleophilic Ring Opening of Donor-Acceptor Azetines: Mechanistic Studies The discovery that the nucleophilic ring opening reaction carried out in DCM requires two molecules of the nucleophile is based on: (1) TIPS-Nuc was isolated as the by-product, and (2) only half of the azetine was converted to product when 1 equiv. of the nucleophile was used. It is not known if loss of the TIPS group and ring opening are sequential or concerted, but it is proposed herein that it is a sequential pathway to show all reaction intermediates, including the 3-azetidiniones (FIG. 4A). The initial abstraction of the silyl (TIPS) group by a nucleophile forms 2-azetine enol E, the tautomer of which is 3-azetidinone carboxylate F. The carbonyl group of F then undergoes attack by the second molecule of the nucleophile to form zwitterionic four-membered ring intermediate G followed by ring opening to the acyclic zwitterion H. Rapid intramolecular proton abstraction by the carbanion forms the final peptide structure. It was attempted to trap intermediate H using benzyl bromide (5 equiv.) or methyl iodide (5-10 equiv.) as the electrophile, but the absence of product from substitution suggested a much higher rate for intramolecular proton transfer. To support this mechanism, deuterium incorporation experiments were carried out on the reaction of 3c with methanol-d$_4$ used as the solvent (FIG. 4B).

The reaction mechanism includes a set of intermediates I-L that are the same to those shown in FIG. 4A. A preparative 0.2 mmol scale ring opening reaction of 3c with methanol-d4 afforded deuterated compound 32 in 92% isolated yield in 2 h without detection of intermediates I-L by the NMR method.26 To investigate a possibility of intermolecular proton transfer from intermediate H to the final product we have performed a competing reaction of 3c with benzylamine and methanol-d4 (FIG. 4C). The formation of 4 as the major product confirmed the intramolecular proton transfer as the major reaction pathway. However, minor amounts of deuterated products were observed in the 1H NMR spectrum of the reaction mixture as the result of deuterium exchange or incorporation from methanol-d4, suggesting competition from intermolecular proton transfer from methanol-d4 during the ring opening. Moreover, diester 32 as the product of reaction of 3c with benzylamine and MeOD was not observed in the reaction mixture.

Example 2. Functionalization of Ring Opened Products

Figures 5A, 5B:
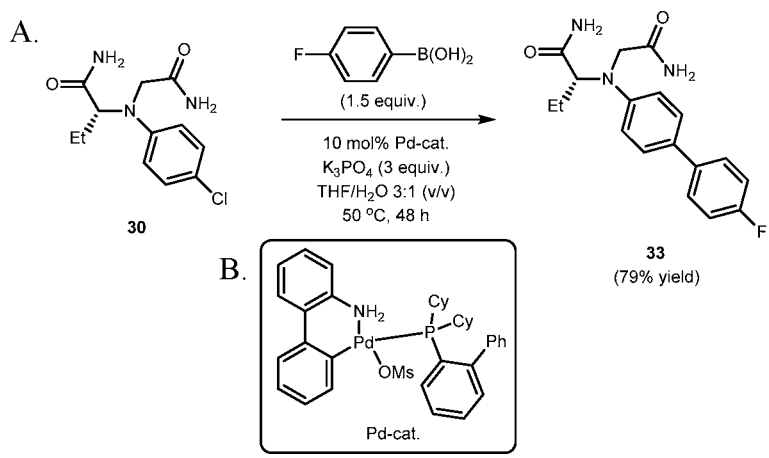
FIG. 5A-5B shows a representative example of Suzuki-Miyaura cross-coupling of a ring opened product.
Figure 5C:
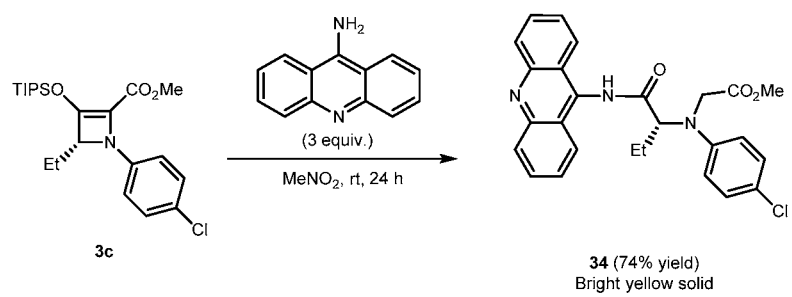
FIG. 5C shows the attachment of fluorescent units to chiral peptides made from functionalization of ring opened products.

To expand the scope of the ring opened products and the synthetic applicability of the chlorine atom attached to the benzene ring, the Suzuki-Miyaura sp$^2$-sp$^2$ cross-coupling with diamide 30 was performed (FIGS. 5A-5B). A compound containing a fluorine atom (diamide 33) was obtained in 79% yield by treatment of diamide 30 with 4-fluorophenylboronic acid using the air and moisture stable Buchwald's third generation precatalyst [a powerful source of Pd(0)] (U.S. Pat. No. 8,889,857) that was synthesized from commercially available precursors. Notably, amide functional groups remained intact under these reaction conditions; however, significant amounts of hydrolysis products were formed at temperatures over 100° C. (conversion of the amide to carboxylates).

The use of fluorophores as sensors is common in chemical biology (Lavis, L. D. & Raines, R. T., *ACS Chem. Biol.* 3, 142-155 (2008); Lavis, L. D. & Raines, R. T., *ACS Chem. Biol.*, 9, 855-866 (2014)) and plays an important role in rapid detection of peptides (Pazos, E., et al., *Chem. Soc. Rev.*, 38, 3348-3359 (2009); Kobayashi, H., et al., *Chem. Rev.*, 110, 2620-2640 (2010); Lee, S., et al., *Biochemistry*, 49, 1364-1376 (2010); Staderinia, M., et al., *Bioorg. Med. Chem.*, 26, 2816-2826 (2018)). Herein, a robust protocol for the attachment of a fluorescent unit using the ring opening reaction of azetine 3c with 4-aminoacridine as a fluorophore-carrying nucleophile is disclosed. Bright yellow chiral dipeptide 34 was obtained in high yield (74%) in nitromethane as the most suitable solvent (FIG. 5B). The UV spectrum of 34 showed maximum absorption at λ=380, 399, and 421 nm; and the fluorescence spectrum showed maximum emission at λ=428, 453, and 480 nm.

Figure 5D:
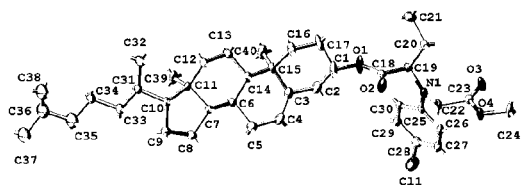
FIGS. 5D-5F shows the functionalization of cholesterol and ergocalciferol (vitamin $D_2$) using chiral peptide attachment. [a]Obtained from 26 (0.2 mmol) and a natural product (0.22 mmol) using N,N'-dicyclohexylcarbodiimide (DCC, 0.24 mmol) and 4-dimethylaminopyridine (DMAP, 0.03 mmol) at room temperature.
Figures 5E, 5F:
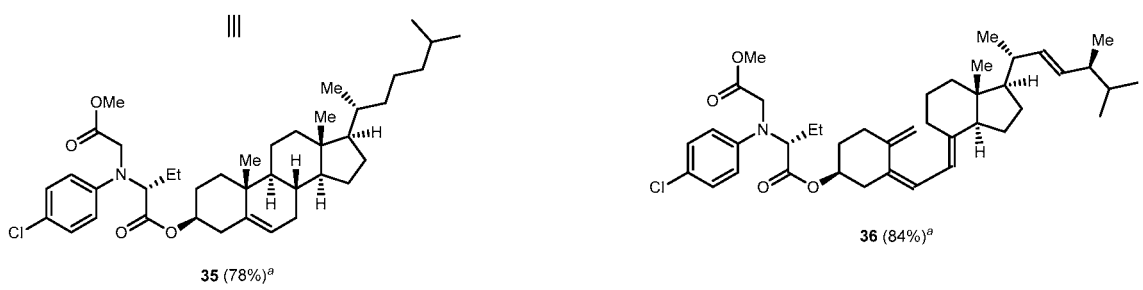

As shown in FIGS. 2A-2F, methanol and primary alcohols, but not secondary alcohols, were suitable for the ring opening of azetines. To solve the problem with secondary alcohols, a two-step protocol was developed: synthesis of chiral monoester 26 and its reaction with naturally-occurring secondary alcohols, cholesterol and ergocalciferol (vitamin D$_2$), using a classic base-catalysed N,N'-dicyclohexylcarbodiimide (DCC) coupling reaction (FIG. 5D-5F). Chiral diester derivatives 35 and 36 were obtained under mild conditions in 78 and 84% yields, respectively, and the structure of 35 was confirmed by X-ray crystallography establishing the absolute configuration of 26 as (R). This experimental evidence allowed the assignment of absolute configurations of all chiral materials—azetines and ring opened products.

The synthesis and transformations of chiral 3-azetidinones as structural analogues of β-lactams have not been previously established. In this work, a highly effective synthetic route to the precursor of this challenging structural unit through the highly enantioselective [3+1]-cycloaddition of silyl-protected enoldiazoacetates with aza-ylides using chiral copper(I) catalysis was reported. The 2-azetidine cycloaddition products undergo generation of 3-azetidinones by reactions with nucleophiles that produce a broad spectrum of peptide products by the retro-Claisen reaction provided by facile strain with high efficacy and complete retention of enantiopurity. This ring opening reaction uncovers a new methodology for the attachment of chiral peptide units to a variety of amines and alcohols, and tolerates a broad scope of nucleophiles including naturally occurring amines, alcohols, amino acids, and other nitrogen based nucleophiles. Mechanistic studies confirm the use of at least two equivalents of a nucleophile for complete and efficient ring opening. Examples of the synthesis of fluorescent dipeptides have been demonstrated using a nitrogen based fluorescent nucleophile for the azetine ring opening. Further functionalization of ring opened products has been successfully performed in the Suzuki cross-coupling and in the esterification of cholesterol and vitamin D2. The mild reaction conditions, high enantiocontrol, broad scope of nucleophiles for the ring opening of donor-acceptor azetines, and ability to perform the reaction in aqueous media demonstrated in this work portray a process that will have wide applications.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for synthesizing donor-acceptor azetines, comprising:
   reacting an enoldiazoacetate with an aza-ylide in the presence of a copper catalyast to produce a donor-acceptor azetine.

2. The method of claim 1, wherein the enoldiazoacetate is

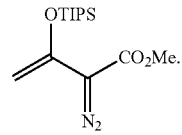

3. The method of claim 1, wherein the aza-ylide is N-arylsulfilimine.

4. The method of claim 1, wherein the copper catalyst comprises Cu(MeCN)$_4$PF$_6$.

5. The method of claim 1, wherein the donor acceptor azetine is methyl 1-(4-chlorophenyl)-3-[(triisopropylsilyl)oxy]-1,4-dihydroazetine-2-carboxylate.

6. The method of claim 1, wherein the reaction further comprises sabox ligand,

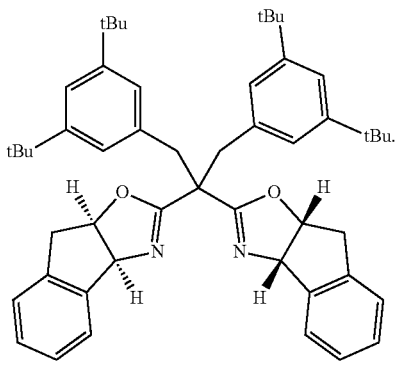

7. A method for producing amino acid derivatives comprising:
   synthesizing donor-acceptor azetines according to the method of claim 1; and
   selectively coupling the donor-acceptor azetine with nitrogen or oxygen nucleophile via 3-azetidinones to form amino acid derivatives.

8. The method of claim 7, wherein the enoldiazoacetate is

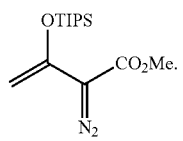

9. The method of claim 7, wherein the aza-ylide is N-arylsulfilimine.

10. The method of claim 7, wherein the copper catalyst comprises Cu(MeCN)$_4$PF$_6$.

11. The method of claim 7, wherein the donor acceptor azetine is methyl 1-(4-chlorophenyl)-3-[(triisopropylsilyl)oxy]-1,4-dihydroazetine-2-carboxylate.

12. The method of claim 7, wherein the reaction further comprises sabox ligand,

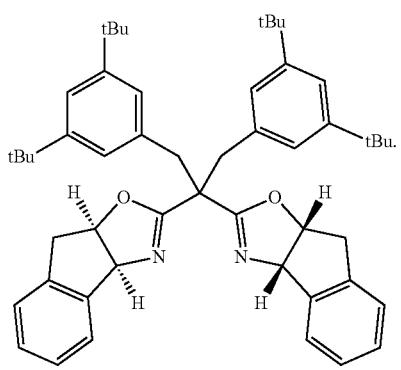

* * * * *